United States Patent
Frigg et al.

(10) Patent No.: US 7,270,682 B2
(45) Date of Patent: Sep. 18, 2007

(54) INTERVERTEBRAL IMPLANT

(75) Inventors: Robert Frigg, Bettlach (CH); Beat Lechmann, Bettlach (CH)

(73) Assignee: Synthes (U.S.A.), West Chester, PA (US)

( * ) Notice: Subject to any disclaimer, the term of this patent is extended or adjusted under 35 U.S.C. 154(b) by 29 days.

(21) Appl. No.: 10/539,658

(22) PCT Filed: Dec. 17, 2002

(86) PCT No.: PCT/CH02/00708

§ 371 (c)(1),
(2), (4) Date: Jul. 11, 2005

(87) PCT Pub. No.: WO2004/054479

PCT Pub. Date: Jul. 1, 2004

(65) Prior Publication Data

US 2006/0009850 A1    Jan. 12, 2006

(51) Int. Cl.
  *A61F 2/44*    (2006.01)
(52) U.S. Cl. .................................................. 623/17.16
(58) Field of Classification Search .. 623/17.11–17.16, 623/16.11, 20.21, 20.23, 20.26; 606/69–70, 606/99; 446/233
See application file for complete search history.

(56) References Cited

U.S. PATENT DOCUMENTS

| 4,759,769 A | 7/1988 | Hedman et al. |
| 5,514,183 A | 5/1996 | Epstein et al. |
| 5,725,597 A | 3/1998 | Hwang |
| 6,402,785 B1 | 6/2002 | Zdeblick et al. |
| 6,610,093 B1 * | 8/2003 | Pisharodi .................. 623/17.15 |
| 2001/0034553 A1 | 10/2001 | Michelson |

FOREIGN PATENT DOCUMENTS

CA    2332822    11/1999

* cited by examiner

*Primary Examiner*—Eduardo C. Robert
*Assistant Examiner*—Michael B Priddy
(74) *Attorney, Agent, or Firm*—Stroock & Stroock & Lavan LLP

(57) ABSTRACT

An intervertebral implant (1), specifically an artificial intervertebral disk, with a central axis (2), and an upper plate-shaped section (10), suitable for laying onto the base plate of a vertebral body lying on top, a lower plate-shaped section (30), suitable for laying onto the cover plate of a vertebral body lying below, wherein a central, plate-shaped section (20) is arranged between the upper and the lower section (10;30), a first circular-cylindrical rod (40) with a longitudinal axle (41) is arranged between the upper section (10) and the central section (20), and a second circular-cylindrical rod (50) with a longitudinal axle (51) is arranged between the lower section (30) and the central section (20).

22 Claims, 12 Drawing Sheets

INTERVERTEBRAL IMPLANT

BACKGROUND OF THE INVENTION

The invention relates to an intervertebral implant according to the generic term of Patent Claim 1 and to a process for the replacement of a defect, natural intervertebral disk by an intervertebral implant.

After removal of a damaged, natural intervertebral disk or a damaged nucleus pulposus of an intervertebral disk, implants or prostheses are inserted into the intervertebral space of two neighbouring vertebral bodies. This suggests the idea of restoring the situation as much as possible to a natural state, i.e. specifically to restore the original height of the intervertebral disk and thus the original distance between the two neighbouring vertebral bodies. Furthermore, the patient should be able to carry out movements of the neighbouring vertebral bodies relative to each other in the natural way, thereby incurring as little obstruction as possible. This essential feature of this system is its ability to retain the freedom of movement in forward/reverse inclination, i.e. flexion and extension of the vertebral bodies, and in lateral bending of the vertebral bodies within the natural limits. The natural sinews and muscles along the spinal column are in general left intact so that they further stabilize the movements of a mechanical intervertebral disk prosthesis.

A characteristic intervertebral disk endoprosthesis is state of the art from DE-A 35 29 761 BÜTTNER. This known intervertebral disk endoprosthesis basically consists of two symmetric closing plates with concave sliding surfaces facing each other, and each having an external surface for laying on the base plate, or the cover plate of the adjoining vertebral body, and a distance piece positioned between the closing plates with convex sliding surfaces arranged complementary to the concave sliding surfaces on the closing plates. The sliding surfaces are designed in one embodiment as section surfaces of a cylinder coat area, wherein the sliding surfaces arranged on the two closing plates are provided complementary to each of the adjoining sliding surfaces at the distance piece, and two complementary sliding surfaces form the articulation surfaces, which can be moved towards each other, of a joint element rotating around a swivel axle. The joint comprises an upper and a lower joint element, each of which has one swivel axle. The two swivel axles are set at 90° to each other. The disadvantages of this known intervertebral disk endoprosthesis is that a) the arrangement of an intervertebral disk endoprosthesis with only one fulcrum does not take sufficient account of the overlaying swivel movements transferred by the natural intervertebral disk, specifically in the anterior-posterior direction and in lateral flexion, which in the natural intervertebral disk are independent of each other;

b) disadvantageous friction forces are generated by two articulating surfaces sliding on each other. This also leads to wear on the surfaces, including also abrasion and resistance in movement of the joint elements. There is also the risk of the "stick slip" effect; and c) a mechanical intervertebral disk prosthesis can scarcely prevent the further degeneration of the affected movement segments. Restoration of the original freedom of movement significantly reduces pain, with the resulting improvement to the patient's quality of life. A review of treatment will, however, have to be undertaken if pain recommences. This will normally involve complete removal of an intervertebral disk prosthesis of the standard model and a stiffening of the movement segment. This operation represents extreme discomfort and strain on the patient.

BRIEF SUMMARY OF THE INVENTION

The invention is intended to remedy this situation. The invention is based on the task of creating an intervertebral implant that comprises a joint, the axles of which are provided with bearings with minimum friction.

The invention solves the task with an intervertebral implant that has the features of Claim 1 and with a process for replacing a defect, natural intervertebral disk by an intervertebral implant.

The advantages achieved by the invention can generally be seen in that with the intervertebral implant according to the invention the swivel movements in the anterior-posterior and the lateral direction are independent of each other;

the friction surface of the movements on the total of four linear contacts is reduced to a minimum; and the linear contact between the joint sections instead of sliding surfaces reduces the friction forces in the joint and as a result relative movement among the vertebral bodies, specifically lateral bending and flexion/extension movement of the spinal column is not impaired.

In a further embodiment of the intervertebral implant according to the invention, two surfaces opposite each other or both pairs of surfaces opposite each other are formed as sliding surfaces for the circular-cylindrical rod(s). These sliding surfaces can thereby be formed as flat, circular-cylindrical or conical surfaces.

The advantages of the different realisations of the sliding surfaces can be found in the flat sliding surfaces allowing the circular-cylindrical rods an unrestricted freedom of movement with an inclination of the neighbouring vertebral bodies relative to each other and with regard to a translation movement of the neighbouring vertebral bodies relative to each other;

concave or specifically circular-cylindrical surfaces mean that sufficient account will be taken of the physiological tilting behavior of the neighbouring vertebral bodies according to the movement segment of the spinal column; and tilted sliding surfaces allow correction of the lordosis or kyphosis to take place at the same time as the operation.

In a further embodiment of the intervertebral implant according to the invention the surfaces on the three plate-shaped sections arranged as sliding surfaces are provided with a peripheral perimeter as security for the rods. This arrangement achieves the advantage of the circular-cylindrical rods being protected by the perimeter against falling out or being squeezed out from the intermediate spaces between the three plate-shaped sections.

In a further embodiment of the intervertebral implant according to the invention, a number of limits/stops are provided for restricting the rotation of the cylindrical rods around the central axle at least on one section of the sliding surfaces. This arrangement allows the following advantages to be achieved:

The rotation of the two rods is limited to a certain direction but with an angular freedom of movement;

This direction can be set to anterio-posterior for the one rod and medio-lateral for the other rod; and It is prevented that the two rods are aligned parallel to each other, so that the joint of the implant would have two parallel swivel axles at a distance from each other and then the two vertebral bodies in the proximity of the intervertebral implant would be able to carry out only flexion/extension movements and no lateral bending or vice versa.

In another embodiment, a pair of grooves is provided on one or both of the sliding-surface pairs formed by the four sliding surfaces as a bearing for the first and/or second rod. Each pair of grooves is preferably congruent to the circular-cylindrical rods it has to bear. The advantage of this embodiment is that the positioning of the grooves ensures that the gradient of the neighbouring vertebral bodies can only be strictly set in the specified directions, such as lateral slant, as well as flexion and extension. Transverse forces that could have an effect on the vertebral joints, can be collected by the intervertebral implant since no translation movements of the plate-shaped sections bordering on the vertebral bodies is possible.

In another embodiment, at least one pair of grooves is designed incongruent to the circular-cylindrical rods they have to bear and is preferably provided with a width that allows a restricted rotation of the rods around the central axle in the grooves. The advantage of this embodiment lies in the restriction is gives to the freedom of movement of the neighbouring vertebral bodies with gradient. Translation is at the same time possible in a strictly lateral or strictly antero-posterior direction.

In a further embodiment, at least one part of the grooves is provided with a limit/stop to prevent against axial shifting of the rod carried by the groove, which stop is attached on the periphery. The grooves preferably do not lead into the side surfaces of the plate-shaped sections but are closed at their ends. This will ensure that the circular-cylindrical rods cannot slip out of the grooves parallel to their longitudinal axes.

The one pair of grooves for the first rod runs preferably from the ventral to the dorsal side surfaces of the corresponding plate-shaped sections whereas the second pair of grooves for the second rod runs between the lateral side surfaces of the corresponding plate-shaped sections.

The antero-posterior orientation of the longitudinal axis of the first rod and the lateral orientation of the longitudinal axis of the second rod results in a joint with crossed swivel axles. The grooves are preferably arranged in such a way that in one case the rod with the longitudinal axis oriented in an antero-posterior direction is at the top and the rod with the longitudinal axis oriented in a lateral-lateral direction is below. The reverse is, however, also possible, which can take account of the circumstances that the individual movement segments of the spinal column are provided with naturally different axle positions.

Instead of by grooves, this orientation of the rods can also be carried out by arrangement of the limiters/stops.

In a further embodiment this comprises elastically malleable means that hold together the upper and the lower section with the intermediate central section and the two rods to each other. The elastically malleable means can be springs or elastomer connection elements.

In a further embodiment the four sliding surfaces and the two rods are made of metal.

In a further embodiment of the intervertebral implant according to the invention the four sliding surfaces are made of metal and the two rods are ceramic.

The following dimensions are suitable for the plate-shaped sections and the cylindrical rods:

Length of the circular-cylindrical rods: larger than half the expansion of the sliding surface coming in contact with the rod;
Radius of the circular-cylindrical rods: between 0.3 mm and 5.0 mm;
Cylinder radius of the sliding surfaces: between 12 mm and 140 mm;
Width of the grooves: between 3 mm and 12 mm;
Depth of the grooves: between 0.2 mm and 4.8 mm; and
Angle range of the admissible rotation of the circular-cylindrical rods around the central axle of the intervertebral implant: between 1° and 32°.

In a further embodiment of the intervertebral implant according to the invention, a means can be attached to the three plate-shaped sections from the ventral side areas which fixes the three plate-shaped sections ventral at a specific distance relative to each other. This measure provides the advantage that the three plate-shaped sections for insertion into the intervertebral space can be brought to a position with fixed implant height and can be moved around the joint after insertion into the intervertebral space and can be placed on the base or cover plate of the adjoining vertebral body.

In a further embodiment of the intervertebral implant according to the invention, the means allows temporary blocking of the mobility of the three plate-shaped sections around the joints. This measure provides the advantage that the joints integrated in the intervertebral space can be blocked by a minimum invasive operation. This is particularly advantageous in cases where the patient suffers from post-operative pain, i.e. where degeneration of the affected spinal column segment continues and the surgeon is considering a fusion of the affected vertebra. The means can preferably be attached to the ventral side areas of the three plate-shaped sections. With this subsequent, secondary blocking of the mobility of the three plate-shaped sections around the joints, the intervertebral implant is stiffened and transferred to an arthrodesis implant (fusion cage).

In a further embodiment of the intervertebral implant according to the invention, the means comprises an insert, which can be placed into each depression on the surfaces of the upper and lower plate-shaped section opposite each other. These depressions are preferably provided as dovetail guides that are open on the ventral side areas of the two external plate-shaped sections, so that the ends of the insert arranged complementary to the dovetail guides can be inserted from ventral into the dovetail guides. This provides the advantage that the mobility of the two plate-shaped sections around the joint is blocked due to the positioning of the insert. The rigidity of the blocking can be increased when the dovetail guides are designed so that they are reduced is size towards the central axis of the intervertebral implant, which creates additional wedging of the insert in the dovetail guides.

In a further embodiment of the intervertebral implant according to the invention, the two plate-shaped sections are provided with drill holes for receiving the bone fixation means, specifically bone screws, wherein the drill holes are provided with longitudinal axes that stand perpendicular to the central axis. Preferably two drill holes will pass through one of the two plate-shaped sections from the ventral side area to the apposition surface. The longitudinal axes, if only an axial fixing of the intervertebral implant is provided, will then be able to stand only perpendicular to the central axis from a lateral perspective, or, if fixing of the intervertebral implant with stable angle is provided, will also from a lateral perspective diverge from the inner surfaces of the two plate-shaped sections against the apposition surfaces.

In a further embodiment of the intervertebral implant according to the invention, the drill holes for receiving the bone fixation means are provided with internal threads, which allows additional, rigid fixing of the bone fixation means in the two plate-shaped sections. The drill holes preferably have a conical shape so that a stronger fixing of the bone fixation means to each of the two plate-shaped sections can be achieved by the resulting conical thread connections between the internal threads and the external threads on the heads of the bone fixation means.

The apposition surfaces are preferably of convex shape and provided with a three-dimensional structure, preferably in the form of pyramid elevations. This arrangement of the apposition surfaces takes account of the anatomy of the vertebral body end plates.

The process according to the invention is intended primarily for replacing a defect, natural intervertebral disk by an intervertebral implant and comprises the following steps:

A) blocking of the joint(s) of an intervertebral implant by means of a special device placed in a certain position of the joint;

B) insertion of the intervertebral implant into the intervertebral space to be treated;

C) release and removal of the device inserted into the intervertebral implant for blocking the joint. Blocking the joint provides the advantage that the moveable plate-shaped sections with the external apposition surfaces can be inserted more easily into the intervertebral space to be treated.

In a further application of the process according to the invention, this comprises the subsequent blocking of the joint on the implanted intervertebral implant by means of the device intended for blocking the joint. This provides the advantage that if the patient should suffer from post-operative pains or in case of a further degeneration of the movement segment, the joint on the intervertebral implant are blocked post-operative by the insertion of the means intended for this purpose. This subsequent blocking can be achieved with an minimally invasive, preferably a laparoscopic operation. The intervertebral implant then assumes the function of a cage, so that the affected movement segment of the spinal column can be stiffened.

The invention and refinements of the invention are described in more detail below on the basis of a partially schematic illustration of several embodiments.

BRIEF DESCRIPTION OF THE DRAWINGS

FIG. 3b shows a section parallel to the second swivel axle of the embodiment of the intervertebral implant according to the invention illustrated in FIG. 3a;

FIG. 8b shows a section parallel to the second swivel axle of the embodiment of the intervertebral implant according to the invention illustrated in FIG. 7 and FIG. 8a;

FIG. 10b shows a section parallel to the second swivel axle of the embodiment of the intervertebral implant according to the invention illustrated in FIG. 9 and FIG. 10a;

DETAILED DESCRIPTION OF THE INVENTION

Figure 1:
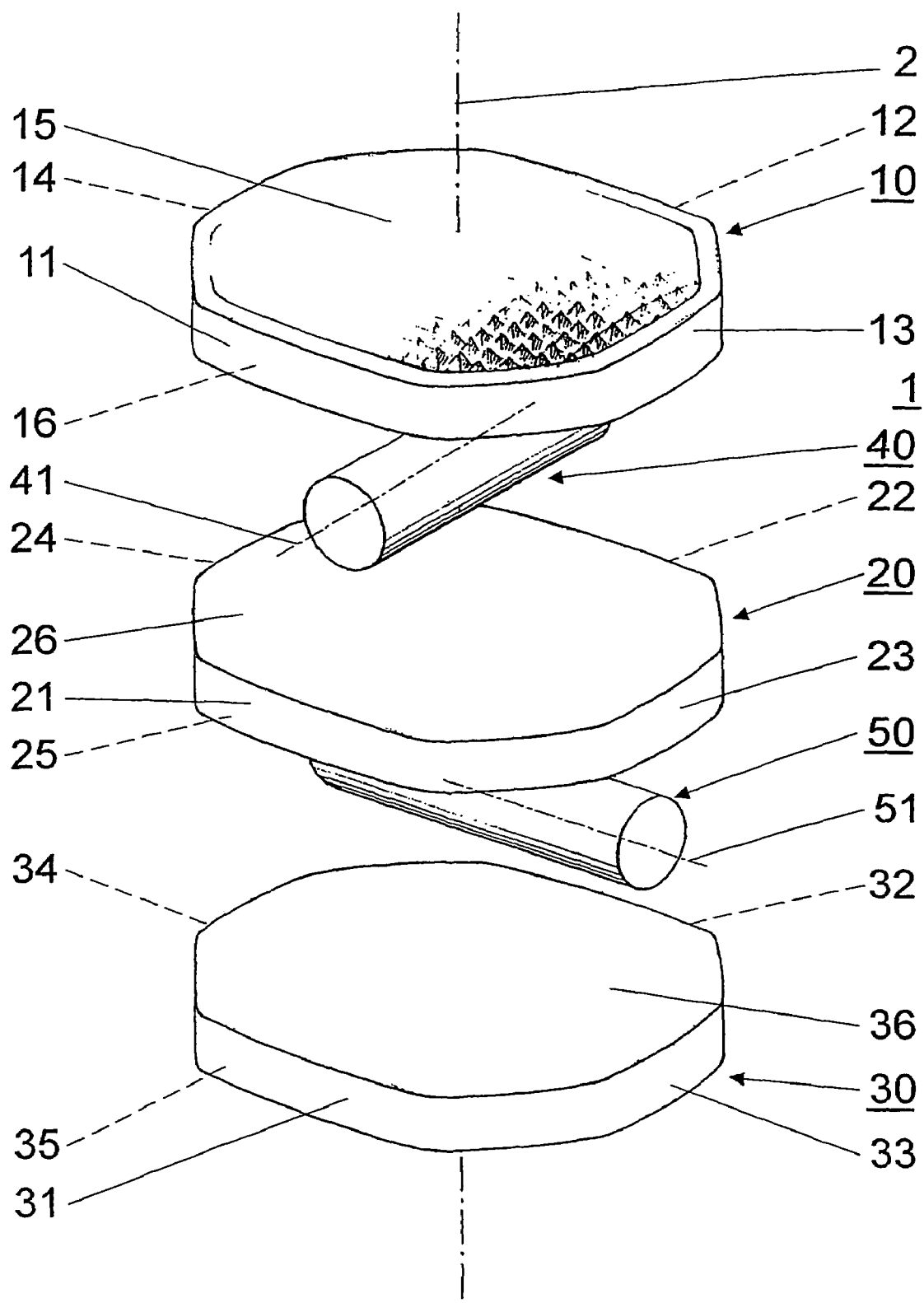
FIG. 1 shows an explosion diagram of one embodiment of the intervertebral implant according to the invention.

An embodiment of the intervertebral implant according to the invention 1 is illustrated in FIG. 1 that comprises with regard to the central axle 2, arranged on top of each other, an upper section 10, with a ventral, a dorsal and two lateral side surfaces 11;12;13;14 as well as an upper apposition surface 15 and a lower surface 16 arranged perpendicular to the central axle 2, a lower section 30, with a ventral, a dorsal and two lateral side surfaces 31;32;33;34, and a lower apposition surface 35 and an upper surface 36 arranged perpendicular to the central axle 2, and a central section 20 positioned between the upper and the lower section 10;30, with a ventral, a dorsal and two lateral side surfaces 21;22;23;24 and towards the lower section 30 with a lower surface 25 and towards the upper section 10 an upper surface 26. The three plate-shaped sections 10;20;30 are provided with an oval, elliptical, circular or polygonal cross-section surface orthogonal to the central axle 2. The surfaces 16;26;25;35 of the three plate-shaped sections 10;20;30 arranged facing each other in pairs are designed here as flat surfaces. A first circular-cylindrical rod 40 is inserted between the upper surface 26 of the central section 20 and the lower surface 16 of the upper section 10. In addition, a second circular-cylindrical rod 50 is inserted between the lower surface 25 of the central section 2 and the upper surface 36 of the lower section 30. The two circular-cylindrical rods 40;50 are arranged between the surfaces 16;26;25;36 so that their longitudinal axes 41;51 are standing vertically to the central axle 2. The circular-cylindrical rods 40;50 arranged between the surfaces 16;26;25;36 lead to the upper section 10 being able to rotate relative to the lower section 30 around the longitudinal axes 41;51 of the circular-cylindrical rods 40;50.

Figure 2A:
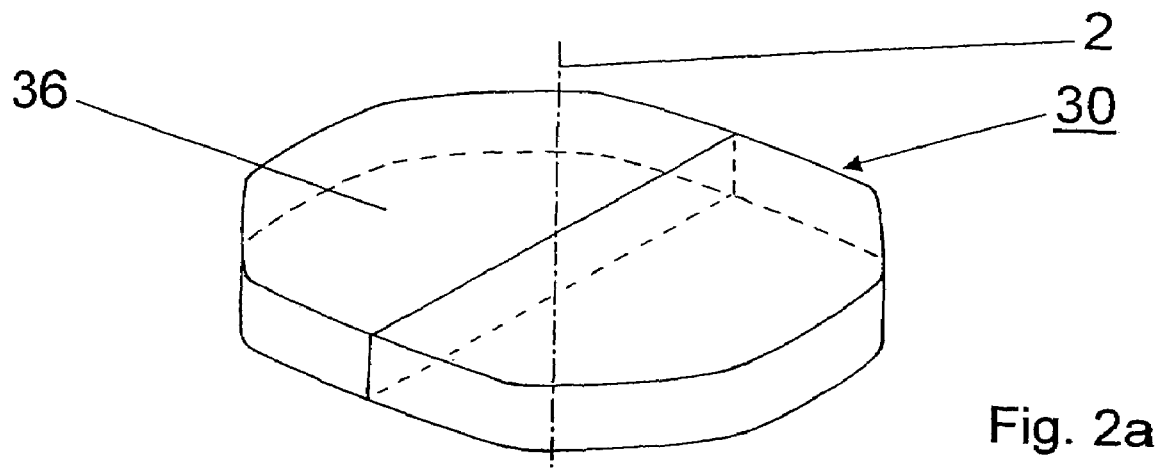
FIGS. 2a-2c shows three perspective illustrations of different embodiments of the sliding surfaces by the example of the lower plate-shaped section.
Figure 2B:
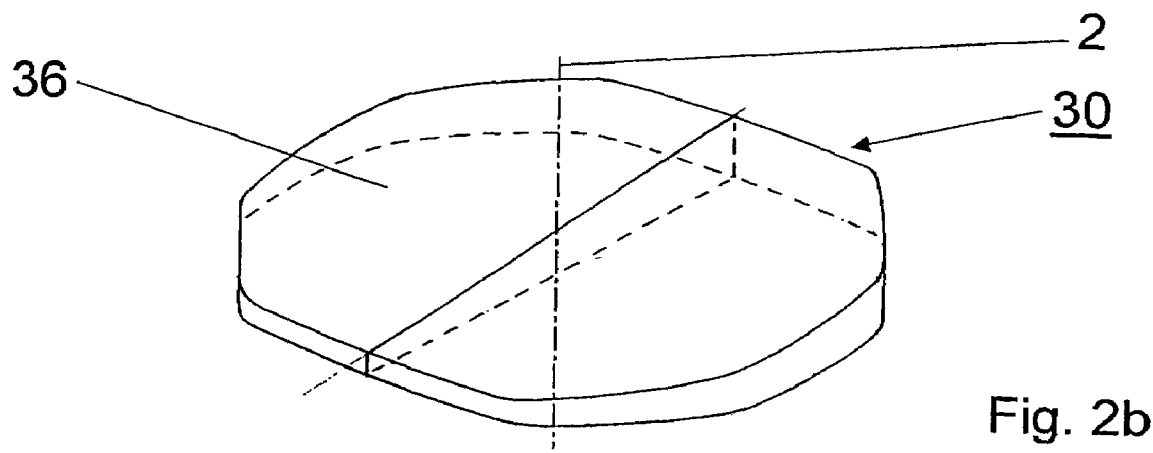
Figure 2C:
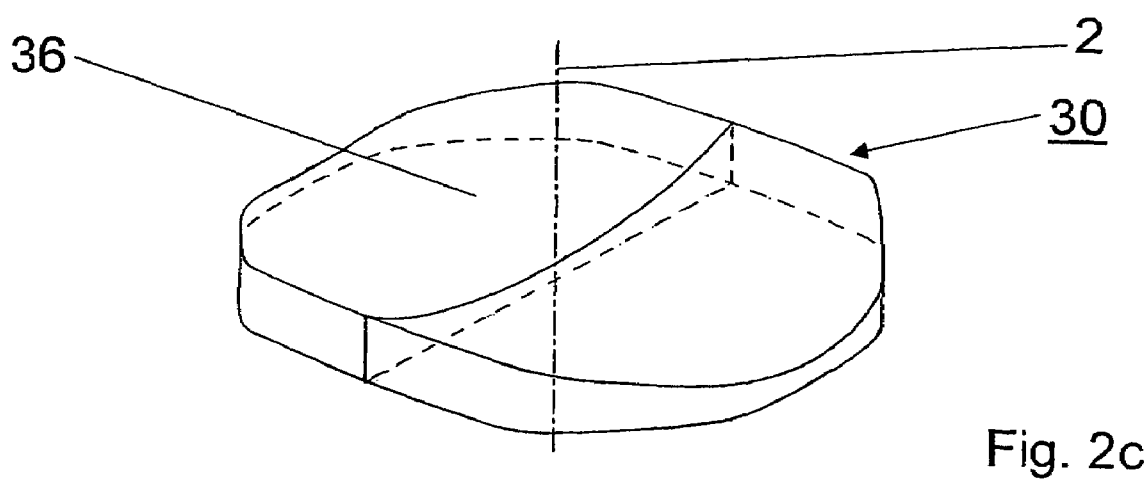

Various embodiments of the surface 36 functioning as a sliding surface are illustrated in FIGS. 2a to 2c by the example of the lower plate-shaped section 30, in which the surface 36 in FIG. 2a is arranged vertically and at a plane to the central axle 2 and in FIG. 2c concave and circular cylindrical. The lower plate-shaped section 30 according to FIG. 2b has a conical design, wherein the surface 36 is arranged at a plane and is not vertical to the central axle 2. The surfaces 16;26;25 of the upper and of the central plate-shaped section 10;20 functioning as sliding surfaces can be arranged in the same way.

Figure 3A:
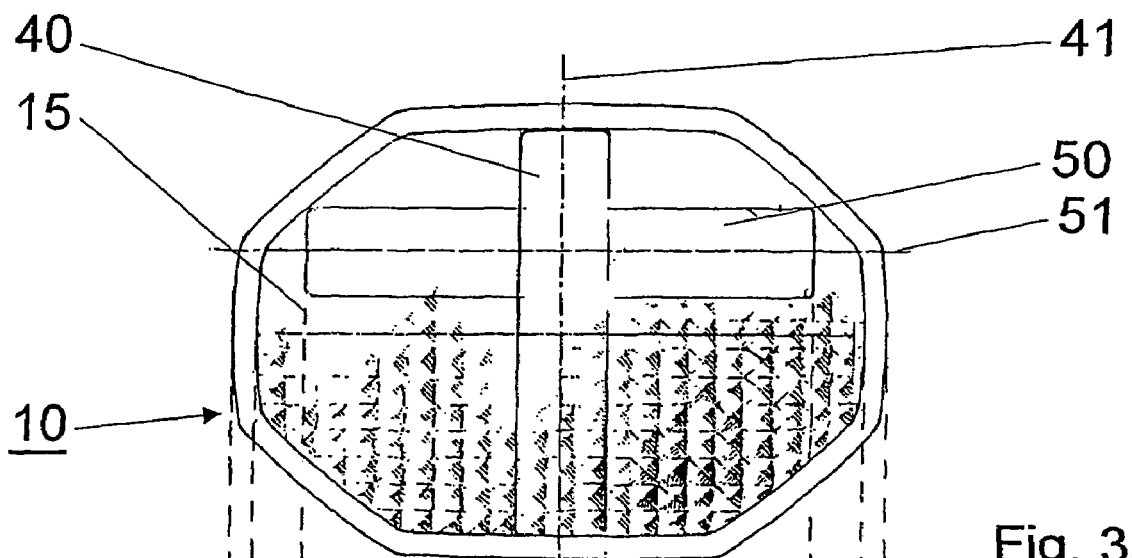
FIG. 3a shows a view of an embodiment of the intervertebral implant according to the invention.
Figure 3B:
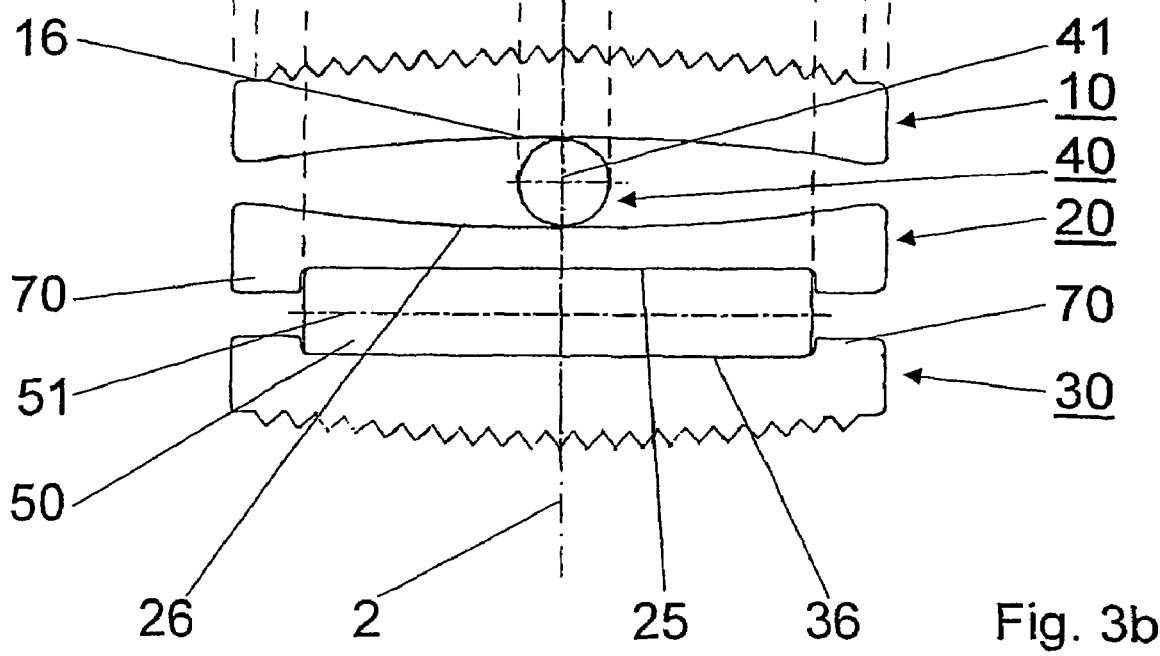

The embodiment of the intervertebral implant according to the invention 1 illustrated in FIG. 3a and FIG. 3b differs from the embodiment illustrated in FIG. 1 only in that the surfaces 16;25;26;36 of the three plate-shaped sections 10;20;30, as illustrated in FIG. 2c, functioning as sliding surfaces are provided with concave and circular-cylindrical arrangement. The surfaces 16;25;26;36 are furthermore arched so that the longitudinal axis 41 of the first circular-cylindrical rod 40 runs antero-posterior and intersects the central axle 2 of the intervertebral implant 1, whereas the longitudinal axis 51 of the second circular-cylindrical rod 50 runs medio-lateral and at a distance from the longitudinal axis 2 of the intervertebral implant 1. The surfaces 16;25; 26;36 are furthermore provided with a partial perimeter 70, which is arranged vertically to the longitudinal axes 41;51 of the two circular-cylindrical rods 40;50, and prevent the shifting of the rods 40;50 parallel to their longitudinal axes 41;51.

Figure 4:
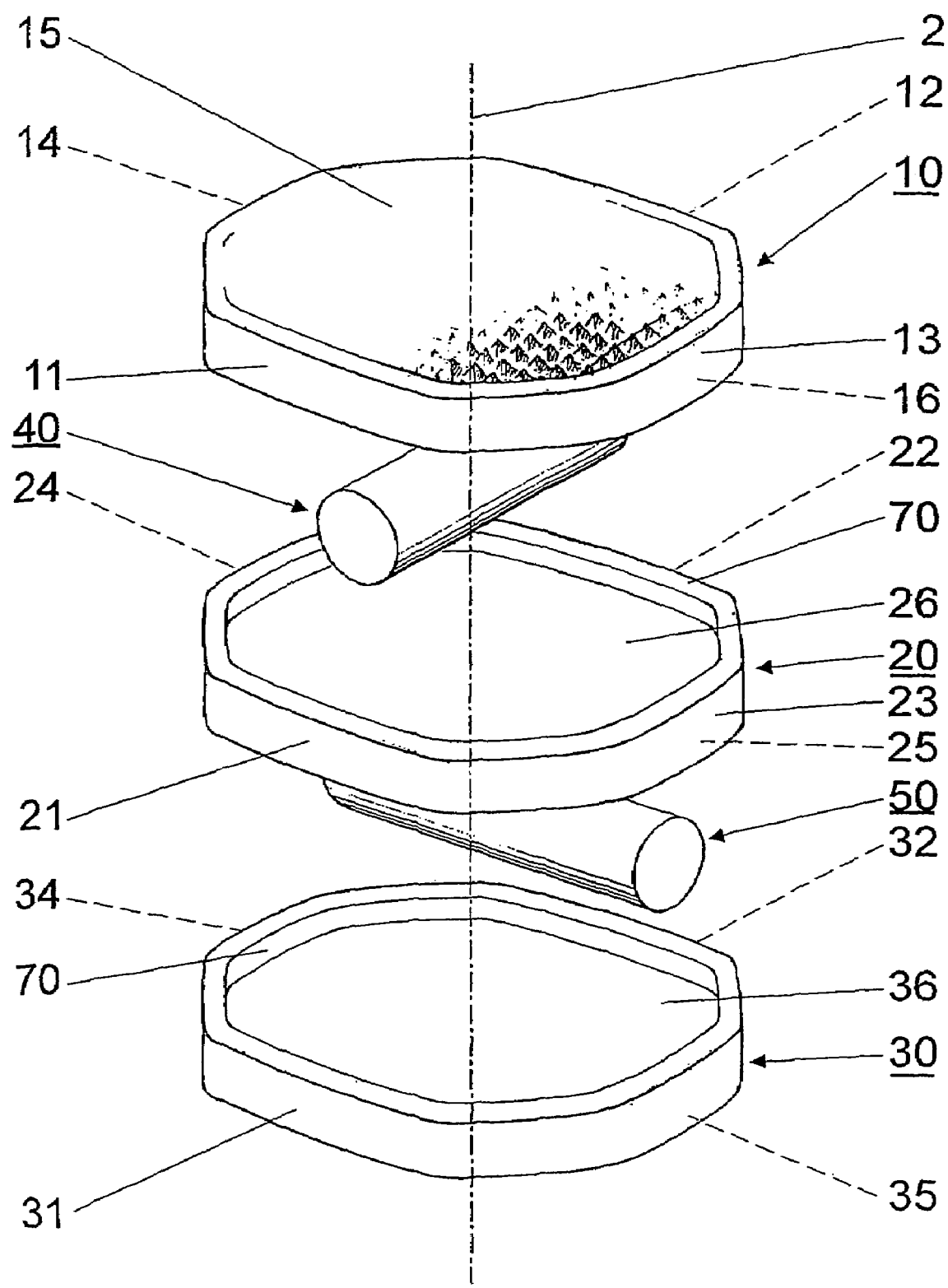
FIG. 4 shows an explosion drawing of a further embodiment of the intervertebral implant according to the invention.
Figure 5:
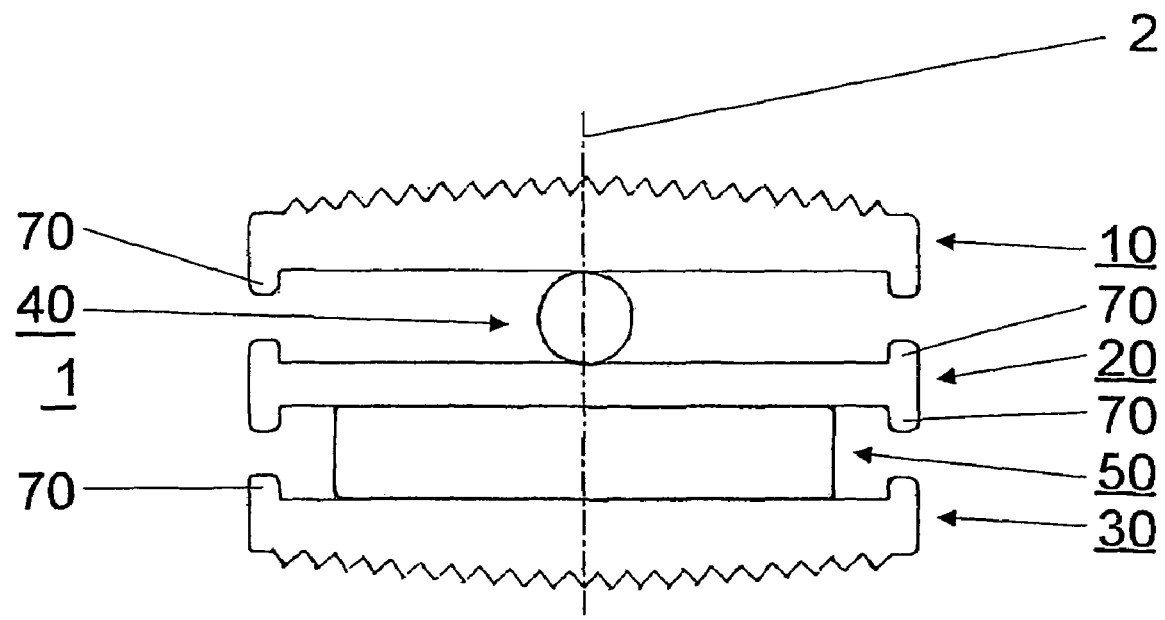
FIG. 5 shows a section parallel to the second swivel axle of the embodiment of the intervertebral implant according to the invention illustrated in FIG. 4.

An embodiment of the intervertebral implant according to the invention is illustrated in FIG. 4 and FIG. 5 that differs from the embodiment illustrated in FIG. 1 only in that the surfaces 16;25;26;36 arranged as sliding surfaces on the three plate-shaped sections 10;20;30 are provided with a peripheral perimeter 70.

Figure 6:
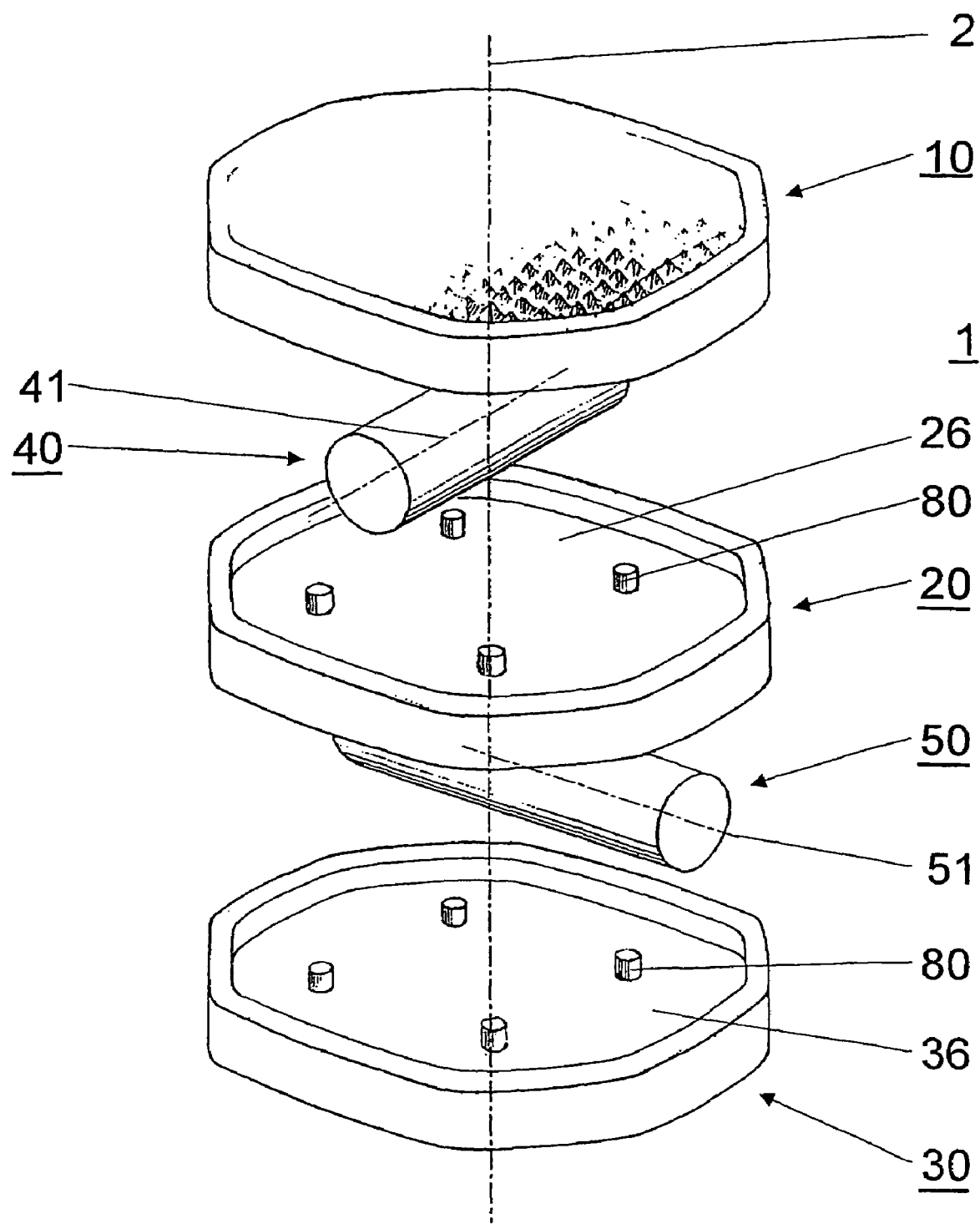
FIG. 6 shows an explosion drawing of a further embodiment of the intervertebral implant according to the invention.

The embodiment of the intervertebral implant according to the invention 1 illustrated in FIG. 6 differs from the embodiment illustrated in FIG. 4 and FIG. 5 only in that four limits/stops 80 are arranged on the upper surface 26 of the central plate-shaped section 20 in order to restrict the movement of the first circular-cylindrical rod 40 between the upper and the central section 10;20 and again four limits/ stops 80 are arranged on the upper surface 36 of the lower plate-shaped section 30 in order to restrict the movement of the second circular-cylindrical rod 50. The limits/stops 80 restricts the swivel angle of the longitudinal axes 41;51 of the two rods 40;50 around the central axle 2.

Figure 7:
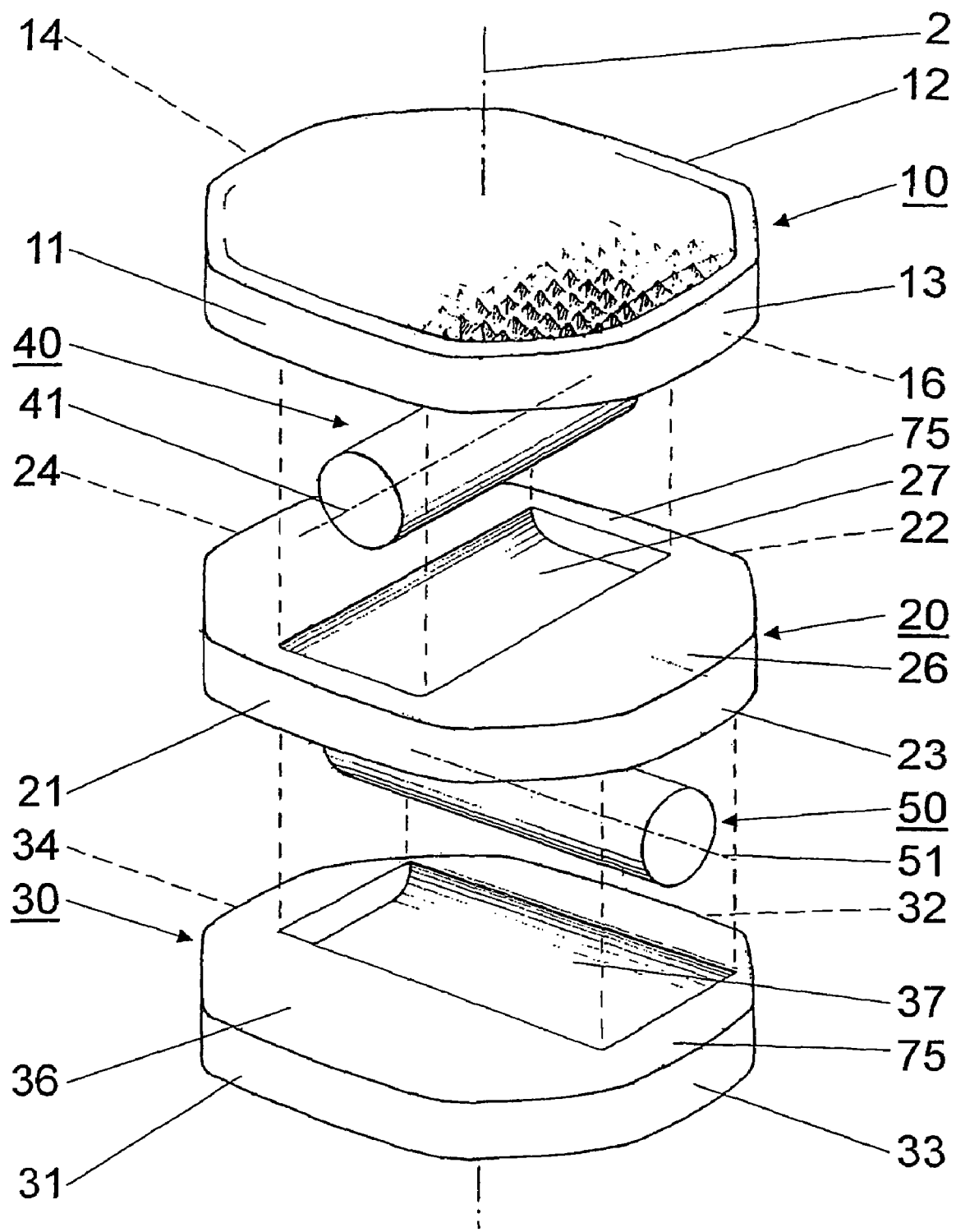
FIG. 7 shows an explosion drawing of a further embodiment of the intervertebral implant according to the invention.
Figure 8A:
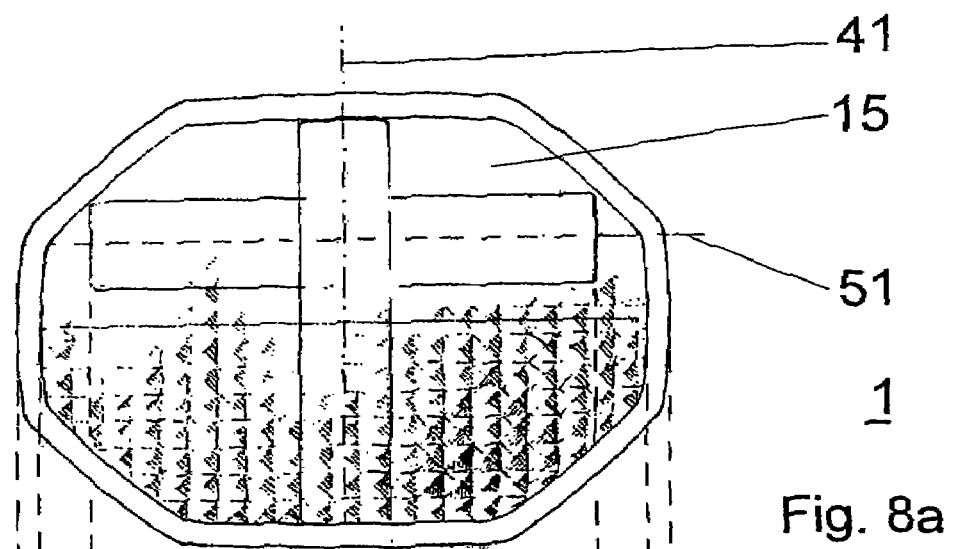
FIG. 8a shows a view of the embodiment of the intervertebral implant according to the invention illustrated in FIG. 7.
Figure 8B:
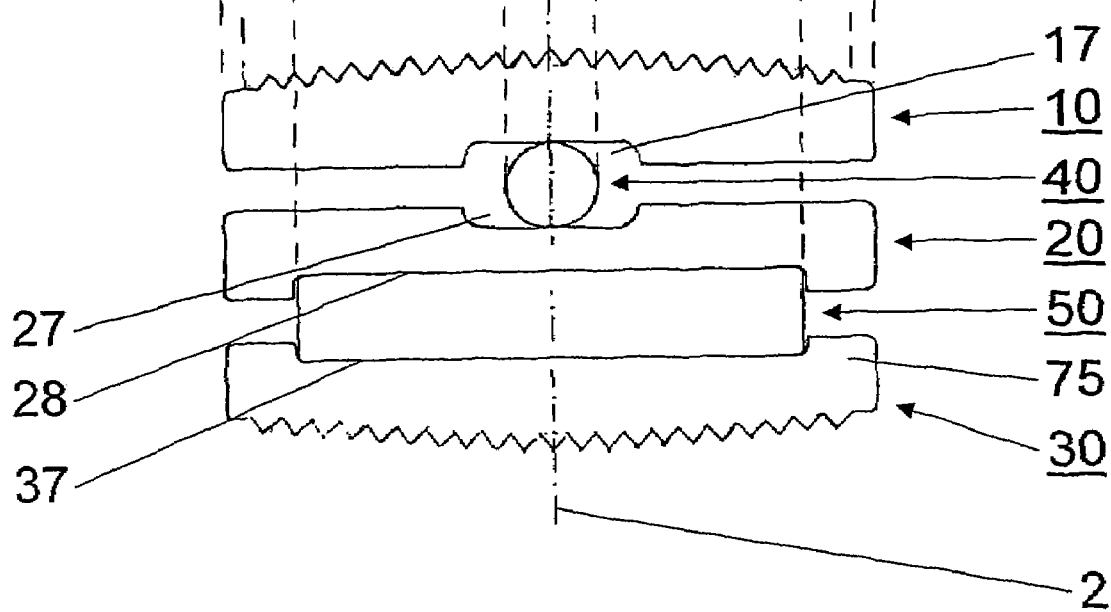

An embodiment of the intervertebral implant according to the invention 1 is illustrated in FIG. 7 and FIG. 8, in which the surfaces 16;26;25;36 of the three plate-shaped sections 10;20;30 assigned to each other in pairs are provided with grooves 17;27;28;37 running perpendicular to the central axle 2. The grooves 17;27;28;37 are used for partial bearing of the circular-cylindrical rods 40;50 and are provided with cross-section surfaces orthogonal to the longitudinal axes 41;51 of the circular-cylindrical rods 40;50, which cross-section surfaces are part areas of an oval. The grooves 17;27 functioning as bearing for the first circular-cylindrical rod 40 are thereby arranged so that the longitudinal axis 41 of the first circular-cylindrical rod 40 runs in an antero-posterior direction. The grooves 28;37 bearing the second circular-cylindrical rod 50 are arranged so that the longitudinal axis 51 of the second circular-cylindrical rod 50 runs in a medio-lateral direction. The grooves 17;27;28;37 are furthermore closed against the side surfaces 11;12;21;22;23; 24;33;34 of the three plate-shaped sections 10;20;30 by means of limits/stops 75, so that the circular-cylindrical rods 40;50 cannot be raised from the grooves 17;27;28;37 parallel to their longitudinal axes 41 ;51. The two circular-cylindrical rods 40;50 are received in part by the grooves 17;27;28;37 so that they are conducted in an axial direction. The grooves 17;27;28;37 are arranged in such a way that the longitudinal axis 41 of the first circular-cylindrical rod 40 running in an antero-posterior direction is arranged diametrically and intersects the central axle 2, whereas the longitudinal axis 51 of the second circular-cylindrical rod 50 running in a medio-lateral direction is set at a distance from the central axle 2.

Figure 9:
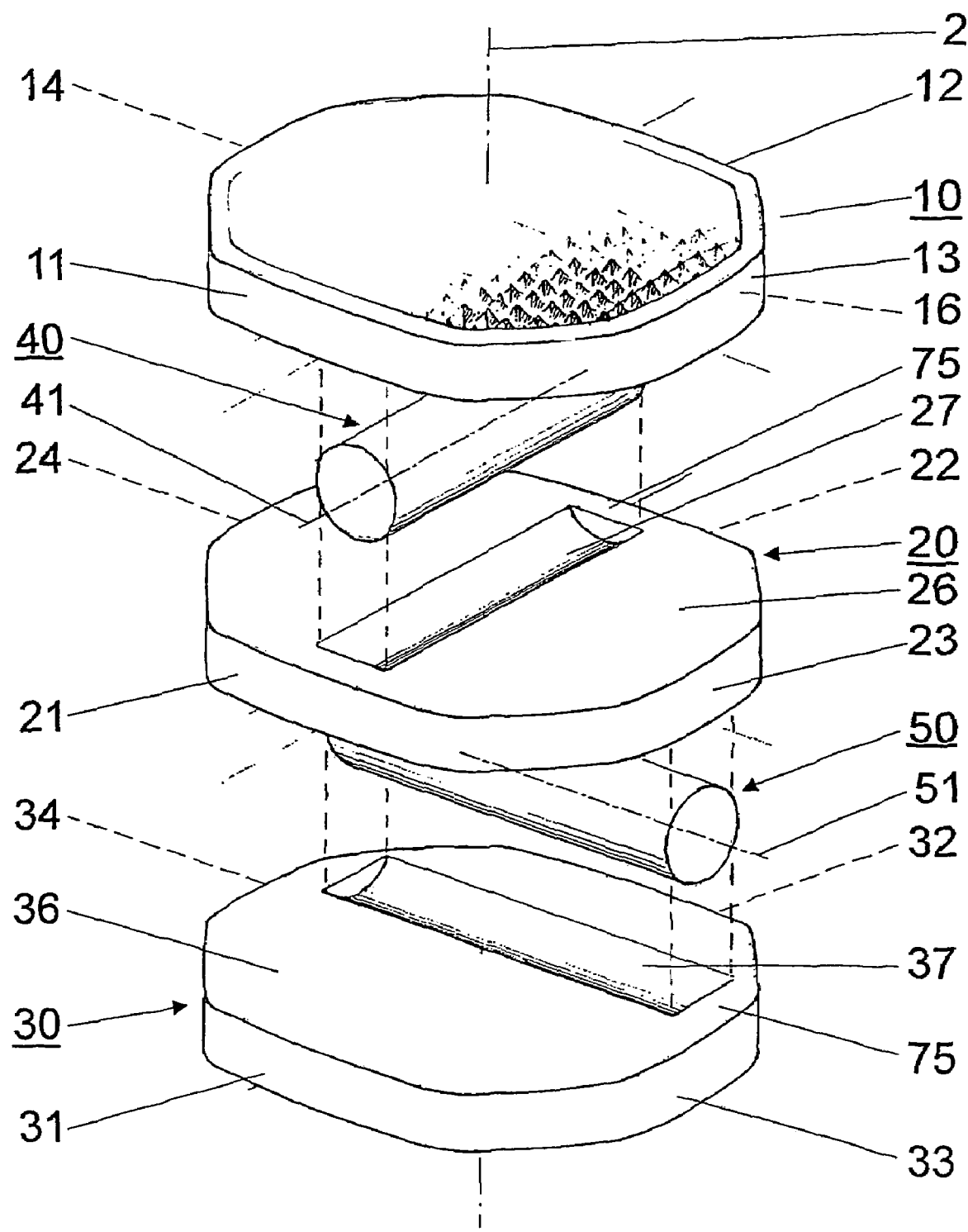
FIG. 9 shows an explosion drawing of a further embodiment of the intervertebral implant according to the invention.
Figure 10A:
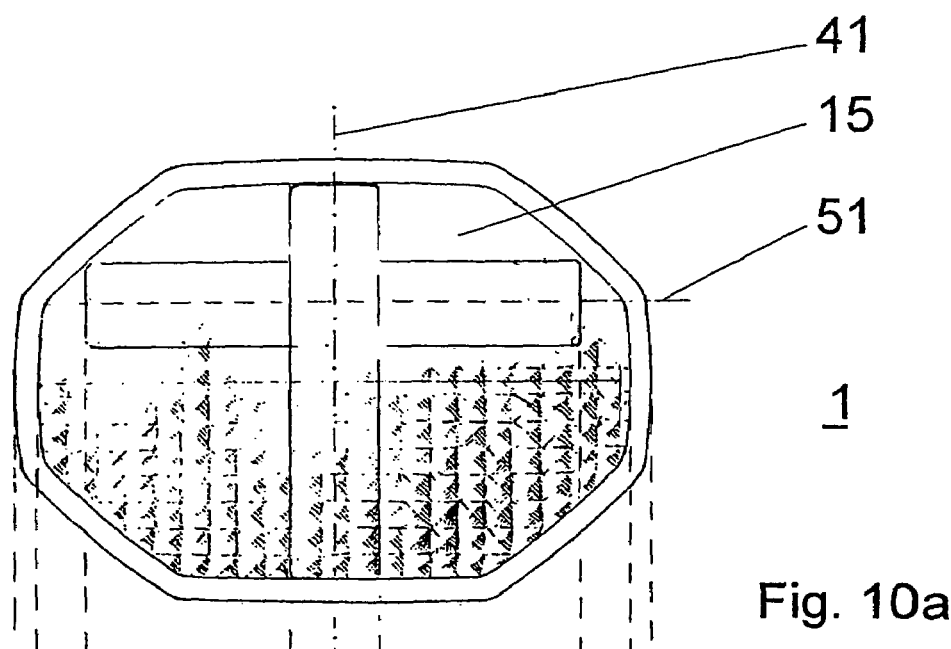
FIG. 10a shows a view of the embodiment of the intervertebral implant according to the invention illustrated in FIG. 9.
Figure 10B:
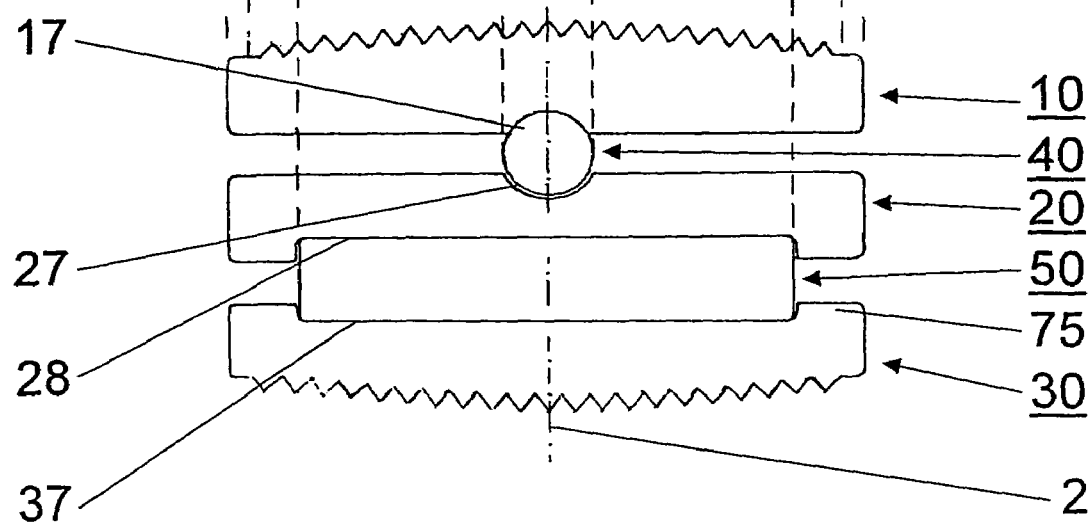

An embodiment of the intervertebral implant according to the invention 1 is illustrated in FIG. 9 and FIG. 10 that differs from the embodiment illustrated in FIG. 7 and FIG. 8 only in that the grooves 17;27;28;37 are provided with a cross-section surface orthogonal to the longitudinal axes 41;51 of the circular-cylindrical rods 40;50, with a circular-segment type of cross-section surface. The two circular-cylindrical rods 40;50 are received in part by the grooves 17;27;28;37, so that they are conducted through the two grooves 17;27;28;37 both axially and perpendicularly to its longitudinal axis 41 and can carry out only a rotation movement around their longitudinal axes 41;51. The grooves 17;27;28;37 are arranged in such a way that the longitudinal axis 41 of the first circular-cylindrical rod 40 running in an antero-posterior direction is arranged diametrically and intersects the central axle 2, whereas the longitudinal axis 51 of the second circular-cylindrical rod 50 running in a medio-lateral direction is set at a distance from the central axle 2.

Figure 11:
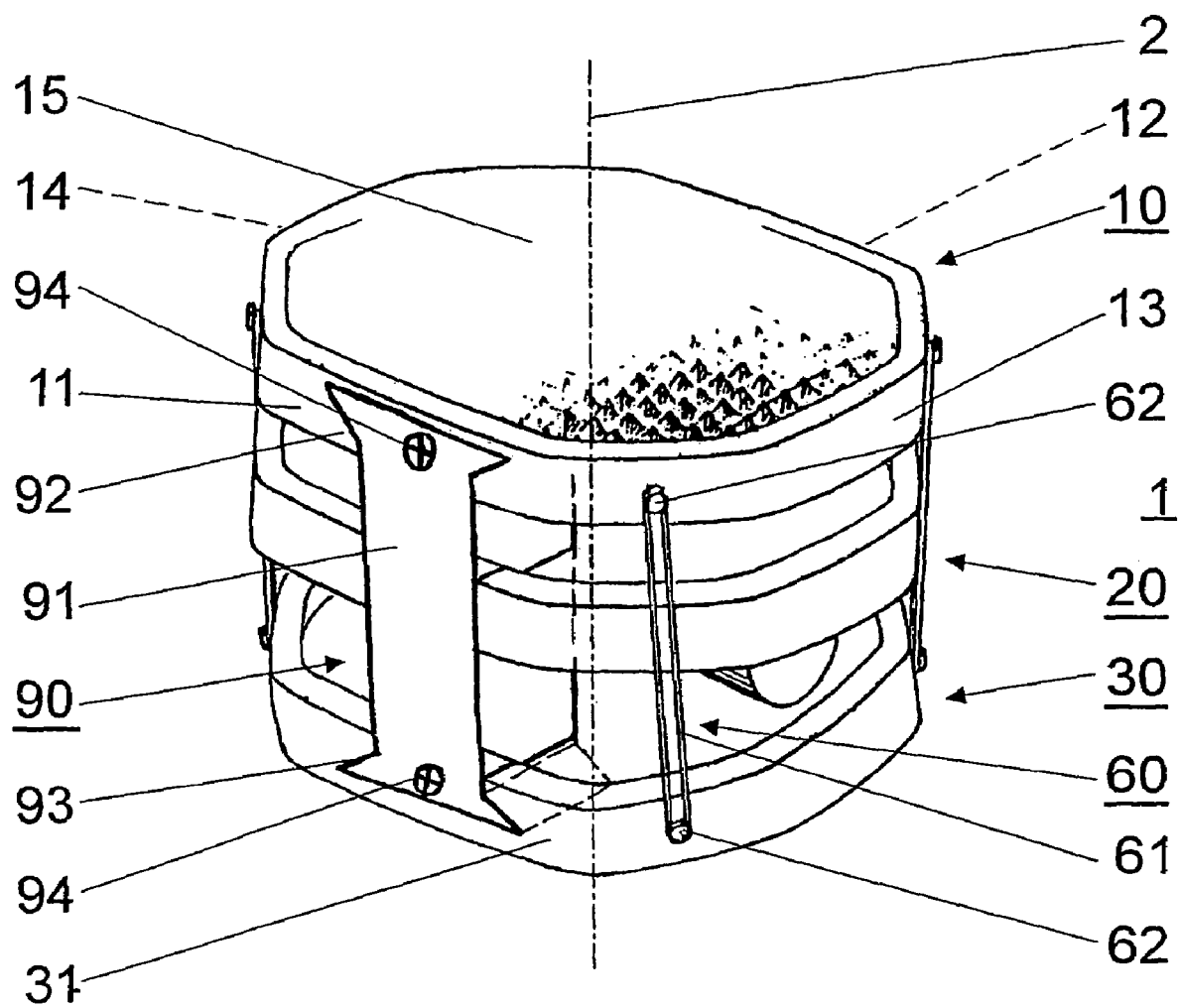
FIG. 11 shows a perspective view of a further embodiment of the intervertebral implant according to the invention.

An embodiment of the intervertebral implant is illustrated in FIG. 11 that differs from the embodiments illustrated in FIGS. 1 to 10 in that the intervertebral implant 1 also comprises means 90, wherein the mobility of the three plate-shaped sections 10;20;30 relative to each other is blocked in a way that can be released. The means 90 in the embodiment illustrated here comprise an insert 91 that can be slid in from the ventral side perpendicular to the central axle 2 and parallel to the lateral side surfaces 13;14;23;24; 33;34 of the three plate-shaped sections 10;20;30. The insert 91 is slid in this way in two depressions 92;93, which are arranged as dovetail guides. The insert 91 is inserted from the ventral side surfaces of the two external plate-shaped sections 10;30 into the depressions 92;93, realized as dovetail guides and secured to two plate-shaped sections 10;30 by means of a screw 94 in each case. The insert 91 is moreover arranged terminally complementary to the depressions 92;93, so that the two external plate-shaped sections 10;30 are fixed parallel to the central axle 2 relative to each other when the insert 91 is in position. The intervertebral implant 1 arranged as springs 61 furthermore comprises elastically malleable means 60, by means of which the three plate-shaped sections 10;20;30 are held together parallel to the central axle 2. The axial elastic malleability of the elastically malleable means 60 ensures there is no restriction on the mobility of the three plate-shaped sections 10;20;30 around the longitudinal axes 41;51 of the two circular-cylindrical rods 40;50 functioning as swivel axles. The springs 61 are arranged as tension springs and secured to catches 62 that are attached to the side surfaces 11;12;13; 14;31;32;33;34 of the two external plate-shaped sections 10;30.

Figure 12:
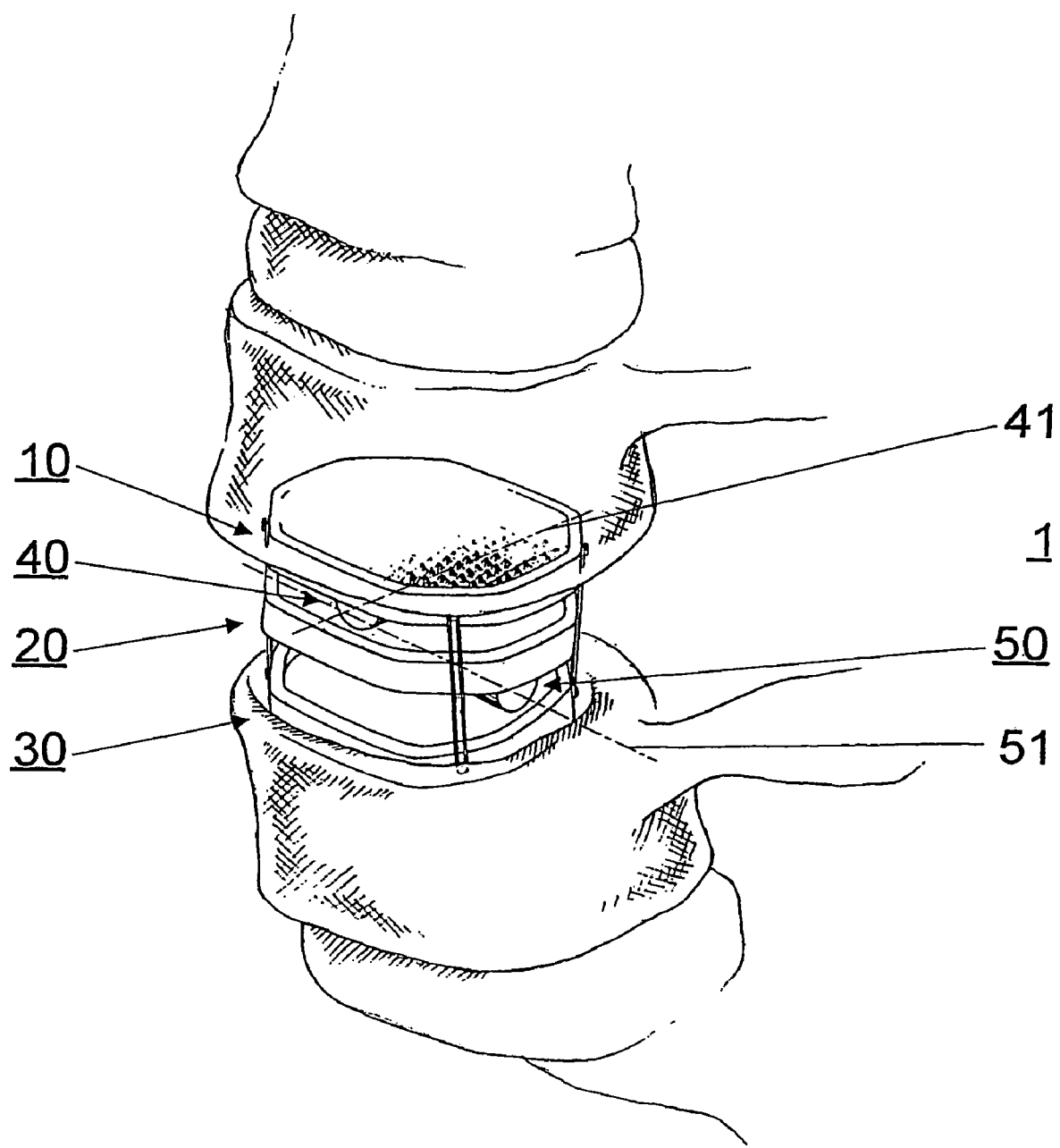
FIG. 12 shows a perspective view of an embodiment of the intervertebral implant according to the invention in the implanted state.

FIG. 12 shows an embodiment of the intervertebral implant 1 implanted between two vertebral bodies bordering on each other. The orientation of the three plate-shaped sections 10;20;30 is such that the longitudinal axis 41 of the first circular-cylindrical rod 40 runs anterior-posterior and the longitudinal axis 51 of the second circular-cylindrical rod 50 runs lateral-lateral.

The invention claimed is:

1. An intervertebral implant, specifically an artificial intervertebral disk, for implantation between adjacent vertebral bodies, each of said vertebral bodies having an endplate, the implant comprising a central axis and A) an upper plate-shaped section, suitable for contacting said endplate of said vertebral body lying above, wherein the upper plate-shaped section is provided with one ventral side surface, one dorsal side surface, two lateral side surfaces, an upper surface and a lower surface;

B) a lower plate-shaped section suitable for contacting said endplate of said vertebral body lying below, wherein the lower plate-shaped section is provided with one ventral side surface, one dorsal side surface, two lateral side surfaces, an upper surface and a lower surface, C) a central plate-shaped section arranged between the upper plate-shaped section and the lower plate-shaped section, wherein the central plate-shaped section is provided with a ventral side surface, a dorsal side surface, two lateral side surfaces, a lower surface facing the lower plate-shaped section and an upper surface facing the upper plate-shaped section;

D) a first circular-cylindrical rod located between the upper plate-shaped section and the central plate-shaped section, the first circular-cylindrical rod being arranged in an anterior posterior orientation; and E) a second circular-cylindrical rod located between the lower plate-shaped section and the central plate-shaped section, the second circular-cylindrical rod being arranged in a medio-lateral orientation.

2. The intervertebral implant according to claim 1, wherein the lower surface of the upper plate-shaped section and the upper surface of the central plate-shaped section form a first sliding surface for the first, circular-cylindrical rod.

3. The intervertebral implant according to claim 2, wherein the first sliding surface for the first circular-cylindrical rod has a concave and circular-cylindrical arrangement.

4. The intervertebral implant according to claim 2, wherein the lower surface of the central plate-shaped section and the upper surface of the lower plate-shaped section form a second sliding surface for the second, circular-cylindrical rod.

5. The intervertebral implant according to claim 4, wherein the second sliding surface for the second, circular-cylindrical rod has a concave and circular-cylindrical arrangement.

6. The intervertebral implant according to claim 4, wherein at least one of the first and second sliding surfaces is provided at least partially with an edge formed on a perimeter of at least one of the upper, lower or central plates for restricting the movement of at least one of the first and second, circular-cylindrical rods.

7. The intervertebral implant according to claim 4, further comprising at least one stop on one or more of the sliding surfaces for restricting the movement of the cylindrical rods.

8. The intervertebral implant according to claim 7, wherein the at least one stop is arranged so that the longitudinal axis of the first rod intersects the ventral and dorsal side surfaces of the corresponding plate-shaped sections and that the longitudinal axis of the second rod intersects the lateral side surfaces of the corresponding plate-shaped sections.

9. The intervertebral implant according to claim 4, further comprising a pair of grooves formed in at least one of the first and second sliding surfaces, the pair of grooves being sized and configured to receive one of the rods.

10. The intervertebral implant according to claim 9, wherein the pair of grooves is congruent to the circular-cylindrical rod carried therein.

11. The intervertebral implant according to claim 9, wherein the at least one pair of grooves is designed incongruent to the circular-cylindrical rod it has to bear and wherein the at least one pair of grooves is provided with a width that allows limited rotation of the rod carried therein.

12. The intervertebral implant according to claim 9, wherein at least one of the grooves is provided with a stop to prevent axial shifting of the rod carried therein.

13. The intervertebral implant according to claim 9, wherein the one pair of grooves for the first rod runs from the ventral to the dorsal side surfaces of the corresponding plate-shaped sections and the second pair of grooves for the second rod runs between the lateral side surfaces of the corresponding plate-shaped sections.

14. The intervertebral implant according to claim 4, wherein the first and second sliding surfaces and the first and second rods are made of metal.

15. The intervertebral implant according to claim 4, wherein the first and second sliding surfaces are made of metal and the first and second rods are made of ceramic.

16. The intervertebral implant according to claim 1, further comprising elastically malleable means for holding the upper and lower plate-shaped sections together with the central plate-shaped section and the two rods.

17. The intervertebral implant according to claim 16, wherein the elastically malleable means are springs or elastomer connection elements.

18. The intervertebral implant according to claim 1, further comprising insertion means for temporary restricting the mobility of the three plate-shaped sections relative to each other.

19. The intervertebral implant according to claim 18, wherein the insertion means is connected to the ventral side surfaces of the upper and lower plate shaped sections.

20. The intervertebral implant according to claim 18, wherein the insertion means comprise an insert with a lower end and an upper end, the upper and lower plate shaped sections each including a depression, which are open on the ventral side surfaces of the upper and lower plate-shaped sections, the depressions being sized and configured to receive the upper and lower ends of the insert.

21. The intervertebral implant according to claim 20, wherein the depressions are dovetail guides and the ends of the insert are arranged complementary to the dovetail guides.

22. The intervertebral implant according to claim 21, wherein the dovetail guides are tapered from the ventral side surfaces of the upper and lower plate-shaped sections towards the dorsal side surfaces of the upper and lower plate-shaped sections.

* * * * *